United States Patent [19]

Chan et al.

[11] 4,016,178

[45] Apr. 5, 1977

[54] SYNTHESIS OF VITAMIN E

[75] Inventors: Ka-Kong Chan, Stanhope; Gabriel Saucy, Essex Fells, both of N.J.

[73] Assignee: Hoffmann-La Roche Inc., Nutley, N.J.

[22] Filed: June 17, 1975

[21] Appl. No.: 587,570

[52] U.S. Cl. .......................... 260/345.5; 260/488 R; 260/526 R; 260/561 R; 260/561 N
[51] Int. Cl.$^2$ ........................................ C07D 311/72
[58] Field of Search ................................ 260/345.5

[56] References Cited

UNITED STATES PATENTS 2,411,967  12/1946  Karrer et al. ................... 260/345.5

OTHER PUBLICATIONS

Hill et al., J. Org. Chem., 37, 3737 (1972).
Sucrow et al., Chem. Ber., 104, 3679 (1971).
Sucrow et al., Chem. Ber., 104, 3689 (1971).

*Primary Examiner*—James O. Thomas, Jr.
*Assistant Examiner*—Nicky Chan
*Attorney, Agent, or Firm*—Samuel L. Welt; Bernard S. Leon; William H. Epstein

[57] ABSTRACT

A synthesis of Vitamin E in racemic or optically active forms from 6-methyl-2-hepten-4-ol; 6,10-dimethyl-2-undecen-4-ol or 6-benzyloxy-2,5,7,8-tetramethyl-chroman-2-acetaldehyde including intermediates in this synthesis.

2 Claims, No Drawings

SYNTHESIS OF VITAMIN E

BACKGROUND OF THE INVENTION

In the past, tocopherol and derivatives thereof which have the formula

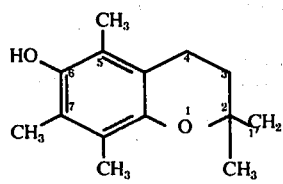

and optically active alpha-tocopherol which is the 2R,4′R,8′R isomer of the compound of formula I, i.e., a compound of the formula

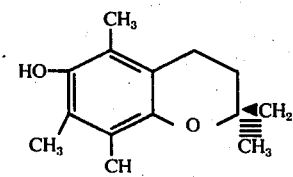

have been prepared through isolation from natural sources such as vegetable oil. This procedure suffers from many drawbacks due to the fact that the tocopherol content of these oils is very small. Therefore, a great amount of oil must be processed in order to isolate a small amount of natural tocopherol. Additionally, the process whereby various tocopherols are isolated from vegetable oil is extremely cumbersome.

Vitamin E active compounds have been synthesized by reacting via Wittig reaction a compound of the formula:

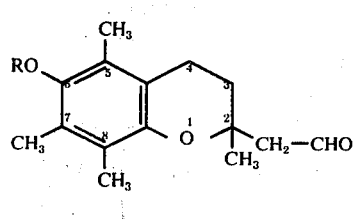

wherein R forms with its attached oxygen moiety an ether protecting group removable by hydrogenolysis or acid catalyzed cleavage; R is preferably benzyl; and a compound of the formula:

III

The compound of formula II can be a racemate or a 2R or 2S isomer, depending upon the desired isomeric form of the compound of formula I.

The compound of formula II can also be a racemate or various 2 and 6, R and S isomers. Where the compound of the formula III has a 2R, 6R configuration, i.e., a compound of the formula

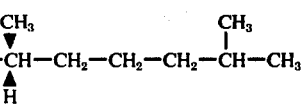

III-A then natural α-tocopherol is produced when the compound of the formula III-A and the 2S isomer of the compound of formula II are utilized.

In accordance with this process, it has been desired to provide a simple and economic method for preparing the compound of formula III and III-A, natural vitamin E and isomers derived therefrom from relatively cheap and economic starting materials.

SUMMARY OF THE INVENTION

In accordance with this invention, it has been found that the compound of the formula

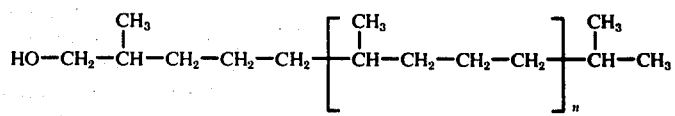

V wherein n is an integer from 0 to 1 can be prepared from a compound of the formula

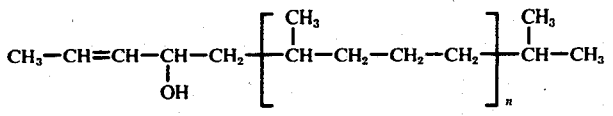

VI wherein $n$ is as above.

The compound of formula V where $n$ is 1 is the compound of formula III. The compound of formula V where $n$ is 0 is compound XXX in Ser. No. 544,163 filed Jan. 27, 1975 and its conversion to the compound of formula III above and vitamin E is disclosed in Ser. No. 544,163, which disclosure is incorporated by reference.

The compound of formula VI above where $n$ is 0 is the compound of formula IX-A and IX-B in U.S. Application Ser. No. 544,153 filed Jan. 27, 1975, Chan and Saucy and the compound of formula VI above where $n$ is 1 is the compound of formula XXIII-A and XXIII-B in U.S. patent application Ser. No. 544,153. The method of preparation for these compounds is disclosed in said U.S. patent application Ser. No. 544,153 which disclosure is incorporated herein by reference.

In accordance with another embodiment of this invention a compound of the formula

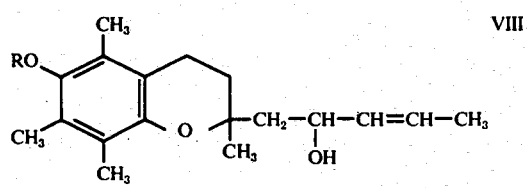

VIII wherein R is as above is converted to a compound of formula I.

DETAILED DESCRIPTION OF THE INVENTION

As used throughout this application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

In the pictorial representation of the compounds given throughout the application, a (▼) tapered line indicates a substituent which is pointed out of the plane of the paper towards the reader.

The term "lower alkoxy" as used throughout the specification denotes lower alkoxy groups containing from 1 to 7 carbon atoms such as methoxy, ethoxy, propoxy, isopropoxy, etc.

As also used herein the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined as above. The preferred aroic acid is benzoic acid.

The term "ether protecting group removable by acid catalyzed cleavage" designates any ether which, upon acid catalyzed cleavage or hydrogenolysis yields the hydroxy group. A suitable ether protecting group is, for example the tetrahydropyranyl ether or 4-methyl-5,6-dihydro-2H-pyranyl ether. Others are arylmethyl ethers such as benzyl, benzhydryl or trityl ethers or alpha-lower alkoxy lower alkyl ether, for example, methoxymethyl or allylic ethers, or trialkyl silyl ethers such as trimethyl silyl ether or dimethyl-tert.-butyl silyl ethers. Other ethers which are preferred are tertiary butyl ethers.

The preferred ethers which are removed by acid catalyzed cleavage are t-butyl and tetrahydropyranyl. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, trifluoroacetic acid, etc. and arylsulfonic acids such as para-toluenesulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The preferred ethers which are removable by hydrogenolysis are the aryl methyl ethers such as benzyl or substituted benzyl ethers. The hydrogenolysis can be carried out by hydrogenation in the presence of a suitable hydrogenation catalyst. Any conventional method of hydrogenation can be utilized in carrying out this procedure. Any conventional hydrogenation catalyst such as palladium or platinum can be utilized.

In accordance with this invention the compound of formula VI is converted to the compound of formula V via th following intermediates:

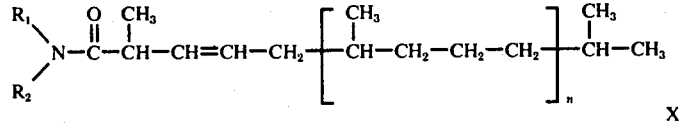

X

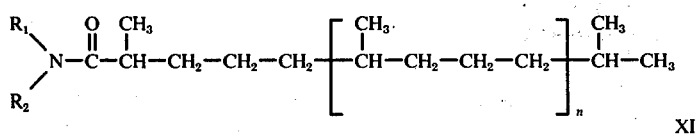

XI

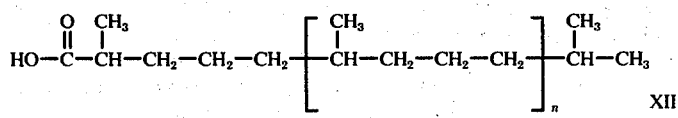

XII

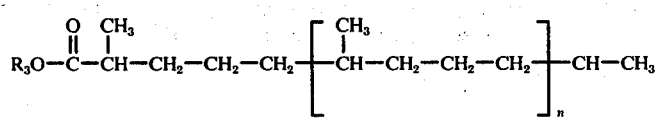

XIII wherein $R_1$, $R_2$ and $R_3$ are lower alkyl and $n$ is as above.

In the reaction of a compound of the formula V to produce a compound of the formula X, the compound of formula VI is reacted with a compound of the formula

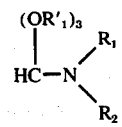

XIV wherein $R_1$ and $R_2$ are as above, and $R'_1$ is lower alkyl.

The reaction of the compound of formula V with the compound of formula XIV is carried out via a rearrangement. In carrying out this reaction, temperatures of from 100° C. to 400° C. are utilized with temperatures of about 150° C. to 250° C. being preferred. This reaction is carried out in an inert organic solvent medium. Among the preferred solvents are the hydrocarbon solvents such as the aliphatic and aromatic hydrocarbons which have a boiling point of at least 100° C. Any conventional inert hydrocarbon solvent having a boiling point of at least 100° C. can be utilized in carrying out this reaction. Among the preferred solvents are the aromatic hydrocarbon solvents such as toluene, xylene, benzene, etc. However, aliphatic hydrocarbon solvents such as octane, hexane, etc. can be utilized in carrying out this reaction. Aliphatic and aromatic amines such as n-tributylamine, collidine, etc. having a boiling point of at least 100° C. can also be used.

The reaction of the compound of formula VI with a compound of the formula XIV produces the rearranged product of formula X.

The compound of formula X is converted to the compound of formula XI by hydrogenation in the presence of a conventional hydrogenation catalyst. Any of the methods of conventionally reducing a double bond to a single bond can be utilized. Among the preferred methods for carrying out this reaction is by hydrogenation in the presence of hydrogenation catalysts such as palladium or platinum. In carrying out this reaction, temperature and pressure are not critical and this hydrogenation can be carried out at room temperature and atmospheric pressure. On the other hand, elevated temperatures and pressures can be utilized.

The compound of formula XI is converted to the compound of formula XII by hydrolysis. Any conventional method of hydrolyzing an amide can be utilized in carrying out this reaction. Among the preferred methods is by treating the amide with an aqueous inorganic acid such as aqueous hydrochloric acid. In carrying out this reaction, temperature and pressure are not critical and this reaction can be carried out at room temperature and atmospheric pressure. On the other hand, elevated temperatures can be utilized.

The compound of formula XII is converted to the compound of formula XIII by esterification. Any conventional method of esterification can be utilized to carry out this reaction. Where $R_3$ is a methyl group, the esterification is carried out under conventional conditions using diazomethane. On the other hand, where it is desired that $R_3$ be a lower alkyl group of from 2 to 7 carbon atoms, the esterification is performed in the conventional manner by reacting a reactive derivative such as a halide or anhydride of the compound of the formula XII with an alcohol.

The compound of formula XIII is converted to the compound of the formula V by reduction. Any conventional method of reducing an ester group to the corresponding alcohol can be utilized. Among the preferred methods of reduction is treating the compound of formula XIII with an aluminum hydride reducing agent. Any of the conventional aluminum hydride reducing agents such as lithium aluminum hydride or diisobutyl aluminum hydride can be utilized in this reaction. Among the other preferred reducing agents are the alkyl aluminum hydride reducing agents such as diisoamyl aluminum hydride, etc., as well as sodium dihydrobis[2-methoxyethoxy]-aluminum hydride. The reduction with an aluminum hydride reducing agent is carried out in an inert organic solvent medium. Any conventional inert organic solvent medium can be utilized for carrying out this reaction. Among the preferred inert organic solvents are included pentane, dioxane, diethyl ether, hexane, toluene, benzene or xylene. Generally, temperatures of from about −120° C. to about 150° C. are utilized in carrying out this reduction reaction.

Where it is desired to produce an opticaly active compound of the formula III-A which is an intermediate for optically active vitamin E, one starts with the compound of formula III in the following isomeric form

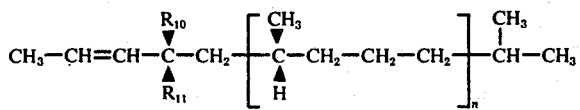

VI-A wherein *n* is as above; one of $R_{10}$ and $R_{11}$ is hydrogen and the other is hydroxy with the proviso that when $R_{10}$ is hydroxy, the 2-3 double bond is a cis configuration and when $R_{11}$ is hydroxy, the 2-3 double bond has a trans configuration to produce an optically active compound of the formula reacted with a compound of the formula XIV occurs asymmetrically to produce a compound of formula X-A which can be converted to optically active natural α-tocopherol of formula I-A. The same optical configuration in the compound of formula X-A is maintained throughout its conversion to produce an optically active isomer of the compound of the formula V, i.e., a compound of formula

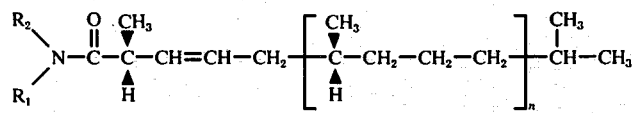

X-A wherein $R_1$, $R_2$ and *n* are as above.

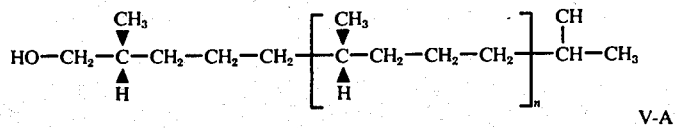

V-A

In accordance with this invention it has been found that when a compound of the formula VI-A is reacted wherein *n* is as above via intermediates of the formulas

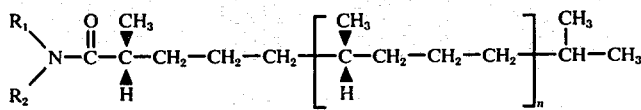

XI-A

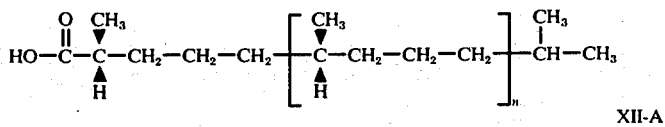

XII-A and

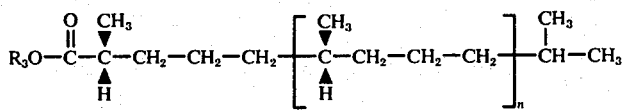

XIII-A in the aforementioned manner with a compound of the formula XIV, the optically active compound of formula X-A is produced. Therefore, it has been found that the rearrangement, which occurs when a compound of formula VI-A is utilized as a starting material and is wherein $R_1$, $R_2$ and *n* are as above.

In accordance with another embodiment of this invention, a compound of the formula VIII is converted to a compound of formula I via the following intermediates:

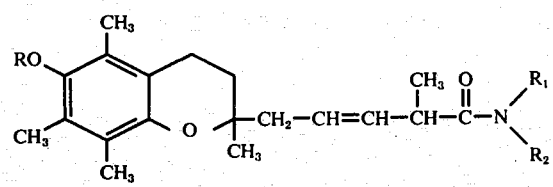

XX

-continued

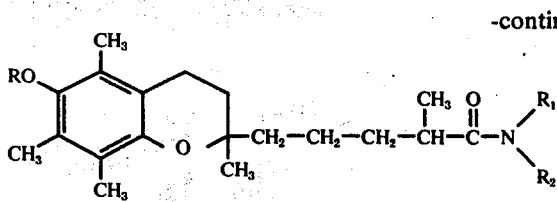

XXI

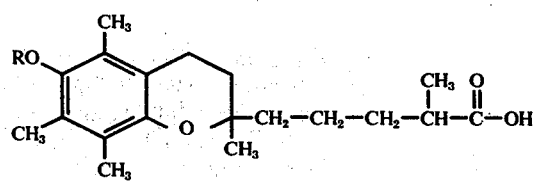

XXII

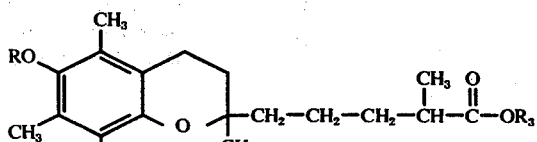

XXIII

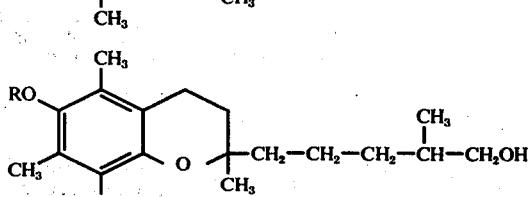

XXIV

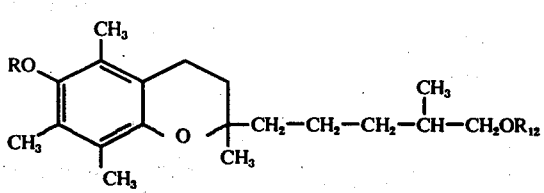

XXV wherein R, $R_1$, $R_2$ and $R_3$ are as above; and $R_{12}$ is a leaving group.

The compound of formula VIII is reacted with the compound of the formula XIV to produce the rearrangement product of formula XX in the same manner as described in connection with the reaction of a compound of the formula XIV with a compound of the formula VI to form a compound of the formula X.

The compound of the formula XX is converted to the compound of the formula XXI in the same manner as described in connection with the conversion of a compound of the formula X to XI. In this conversion, care must be taken that approximately one mole of hydrogen is utilized per mole of the compound of the formula XX so as not to remove the OR moiety where the OR moiety forms an ether group removable by hydrogenolysis. The use of one mole of hydrogen per mole of the compound of formula XX will hydrogenate the double bond without effecting the OR moiety where R forms an ether group removable by hydrogenalysis. In the case, where higher molar ratios of hydrogen are utilized, the hydrogen will attack the OR group forming the corresponding alcohol.

The compound of formula XXI is converted to the compound of formula XXII in the same manner described in connection with the conversion of a compound of the formula XI to a compound of the formula XII. The compound of formula XXII is converted to compound of the formula XXIII in the same manner as described in connection with the conversion of a compound of the formula XII to a compound of the formula XIII.

Either the compound of the formula XII or the compound of the formula XXIII can be converted to a compound of the formula XXIV by reduction with a lithium aluminum hydride reducing agent in the same manner as described hereinbefore with respect to the conversion of a compound of the formula XIII to a compound of the formula V.

The compound of formula XXIV is converted to the compound of formula XXV by converting the hydroxy group in the compound of formula XXIV to a leaving group. Any conventional method of converting a hydroxy group to a leaving group can be utilized in this reaction. Among the preferred leaving groups formed by —$OR_{12}$ are alkyl sulfonyloxy such as method sulfonyloxy or other lower alkyl sulfonyloxy groups; aryl sulfonyloxy such as p-toluene-sulfonyloxy, naphthyl sulfonyloxy, etc.

The compound of formula XXV is converted to the compound of formula I by reacting the compound of formula XXV with a compound of the formula:

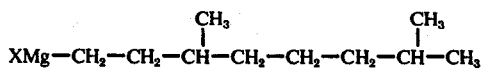

XVI wherein X is halogen; followed by hydrogenalysis or acid hydrolysis to remove the RO-group. The reaction of the compound of formula XXV with a compound of formula XVI is carried out with a di(alkali metal)tetrahalocuprate utilizing the procedure of Fouquet and Schlosser on pages 82 and 83 of Angew Chem International Edit, Vol. 13, 1974. In this procedure, carbon to carbon linkage of hydrocarbons is carried out through the reaction of a magnesium halide with a sulfonyl ester. In accordance with this invention, it has been discovered that this reaction can be carried out with an ether or chromane functional group so that the sulfonyl ester can carry these functional groups. In accordance with this invention, it has been discovered that the ether or chromane groups do not interfere with this reaction. In this reaction, any conventional di(alkali metal) tetrahalocuprate can be utilized with dilithium tetrachlorocuprate being preferred. Generally, this reaction is carried out in the presence of an ether solvent. Any conventional inert organic ether solvent can be utilized. Among the preferred solvents are included tetrahydrofuran, dioxane, diethyl ether, dimethoxyethane, diglyme, etc. In carrying out this reaction, temperature and pressure are not critical and this reaction can be carried out at room temperature and atmospheric pressure.

In accordance with a preferred embodiment of this invention, the compound of formula I-A, i.e., optically active natural α-tocopherol can be prepared through the discovery that the rearrangement of an optically active form of the compound of formula VIII with a compound of formula XIV occurs stereoselectively so that the optical isomer convertible to natural α-tocopherol is produced. Hence in accordance with this invention, we have found that when the optically active form of the compound of formula VIII which has the formula

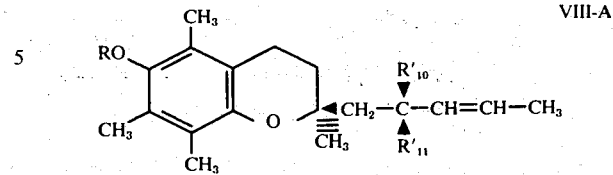

VIII-A wherein R is as above and one of $R'_{10}$ and $R'_{11}$ is hydroxy and the other is hydrogen with the proviso that when $R'_{10}$ is hydroxy the 2-3 double bond is cis and when $R'_{10}$ is hydrogen, the 2-3 double bond is trans is utilized, a compound of formula I-A is produced.

The compound of formula VIII-A is reacted in the aforementioned manner with a compound of the formula XIV to produce a compound of the formula

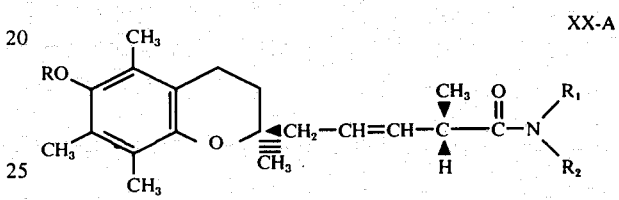

XX-A wherein R, $R_1$ and $R_2$ are as above. The compound of formula XX-A is converted to the optically active form of the compound of formula XXV, i.e., a compound of the formula

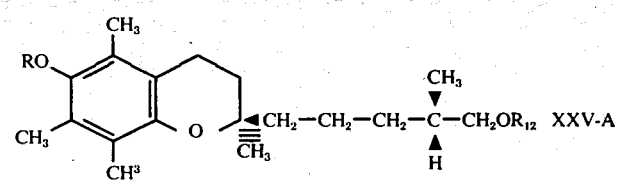

XXV-A wherein R and $R_{12}$ are as above in the manner described hereinbefore via the following compounds:

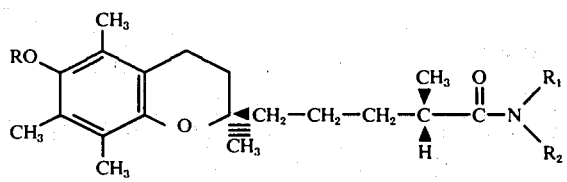

XXI-A

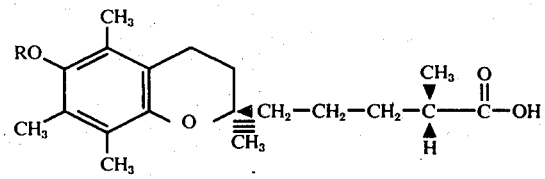

XXII-A

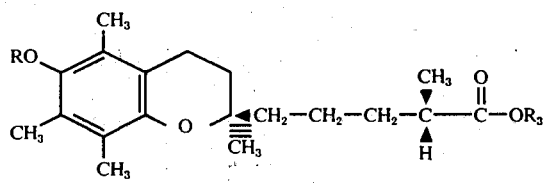

XXXIII-A

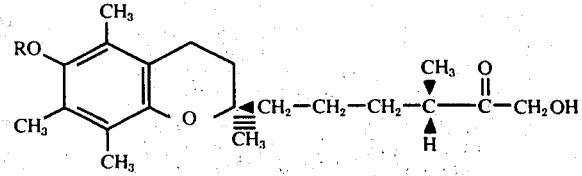

XXIV-A

The compound of formula XXV-A, when reacted with the optically active form of the compound of formula XVI, i.e.,

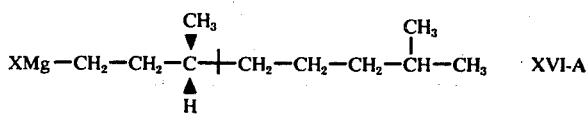
XVI-A wherein X is as above via a Grignard reaction produces the compound of formula I-A in the same manner as described in connection with the reaction of a compound of formula XXV with a compound of formula XVI to produce a compound of formula I.

The compound of formula VIII is formed from a compound of formula II by reaction via a Grignard reaction with a compound of the formula

 XXIX to produce a compound of the formula

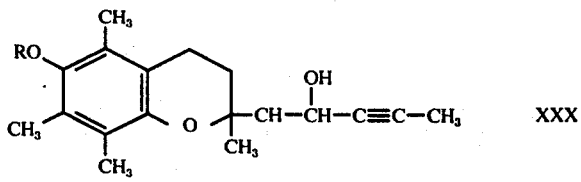 XXX where R is as above; which when subjected to selective hydrogenation or metal hydride reduction produces the compound of formula VIII.

On the other hand, when an optical isomer of the formula II having the formula:

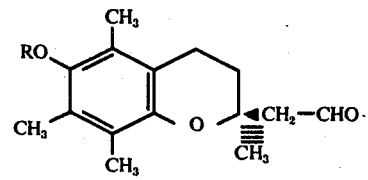 II-A wherein R is as above; is condensed with the compound of formula XXIX, a mixture is formed containing a compound

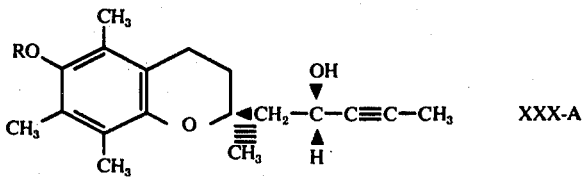 XXX-A and a compound of the formula

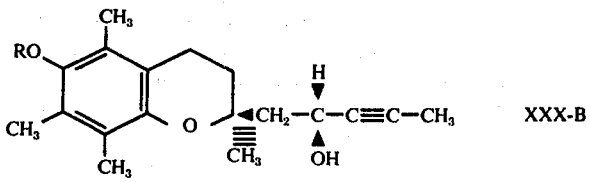 XXX-B wherein R is as above. The compound of formula XXX-A can be converted to a compound of the formula

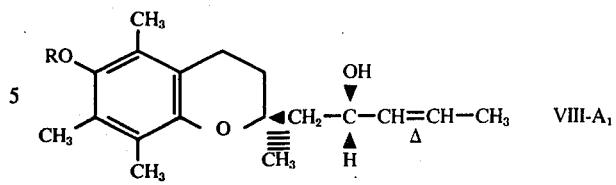 VIII-A$_1$ wherein R is as above and Δ indicates that a double bond has a cis configuration. The compound of formula XXX-B can be converted to a compound of the formula

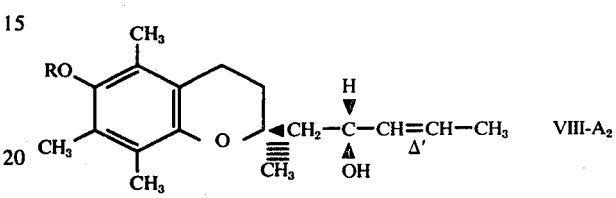 VIII-A$_2$ wherein R is as above and Δ' indicates that the double bond has a trans configuration.

The mixture of the compound of formula XXX-A and XXX-B can be separated by any conventional means such as crystallization.

The compound of formula XXX-A is converted to the compound of the formula VIII-A$_1$ by hydrogenation in the presence of a selective hydrogenation catalyst. Any conventional catalyst which selectively reduces only the triple bond (acetylenic linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium/lead catalyst of the type disclosed in Helvetica Chemica Acta.: 35, page 446 (1952) and U.S. Pat. No. 2,681,938, Lindlar. In carrying out this hydrogenation, temperature is not critical and this reaction can be carried out at room temperature. On the other hand, elevated or reduced temperatures can be utilized. Generally, this reaction is carried out in an inert organic solvent. Any conventional inert organic solvent can be utilized such as n-hexane, ethyl acetate, toluene, petroleum ether or methanol. The selective hydrogenation of a compound of the formula XXX-A utilizing a selective hydrogenation catalyst produces a cis configuration across the double bond formed in the compound of formula VIII-A$_1$. Therefore, the subjection of a compound of the formula XXX to catalytic selective hydrogenation produces a compound of the formula VIII-A$_1$ where the double bond is a cis double bond.

In accordance with this invention, the compound of formula XXX-B is converted to the compound of VIII-A$_2$ by chemical reduction with an aluminum hydride reducing agent. The chemical reduction of the compound of formula XXX-B reduces the triple bond to a double bond which has a trans configuration. Hence, the compound of formula VIII-A is formed by this chemical reduction with the double bond having a trans configuration. The reduction can be carried out by treating the compound of formula XXX-B with an aluminum hydride reducing agent in the manner described hereinbefore. Any of the conventional aluminum hydride reducing agents such as those described hereinbefore can be utilized to carry out this reduction reaction.

The following Examples are illustrative but not limitative of the invention. All temperatures are in degrees Centigrade (° C.) and the ether utilized is diethyl ether. The term "5% palladium on carbon" designates a carbon catalyst containing 5% by weight palladium and 95% by weight carbon. The term "Lindlar catalyst" designates a catalyst prepared from palladium, calcium carbonate and lead acetate as described in Organic Synthesis Collective Volume 5: pages 880–883 (1973). In the Examples, the percent R and S were determined by nmr.

EXAMPLE 1

Preparation of 2(R,S,)-6-dimethyl-3(E)-heptenoic acid dimethylamide 6-methyl-2(Z)-hepten-4(R,S)-ol (1.28 g., 10 mmol) and dimethylformamide dimethyl acetal (7.14 g., 60 mmol) in xylene (20 ml.) were refluxed at 130° C. under the continuous removal of methanol for 20 hours. After evaporation of xylene in a rotary evaporator at 42°/20 mm Hg, the crude oily product was chromatographed on 40 g. of silica gel. Elution with diethyl ether = petroleum ether (30°–60°) (1:3 parts by volume) gave 540 mg. (42.1% by weight) of starting material. Further elution with ether = petroleum ether (11 = 9 parts by volume) afforded 257 mg. of crude product, which on Kugelrohr distillation at 65°–70° C./0.2 mm Hg yielded 200 mg. (18.9%) based on recovered starting material) of 2(R,S),6-dimethyl-3(E)-heptenoic acid dimethylamide as a colorless oil.

EXAMPLE 2

Preparation of 2(R),6-dimethyl-3(E)-heptenoic acid dimethylamide from 6-methyl-2-(Z)-hepten-4(R)-ol Optically active 6-methyl-2-(z)-hepten-4(R)-ol (2.56 g., 20 mmol) (having about 96.5% by weight R and about 3.5% by weight S), dimethylformamide dimethylacetal (15 g., 0.126 mmol) in xylene (40 ml.) were refluxed under continuous removal of methanol for 120 hours. The solvent and excess of reagent were evaporated off in a rotary evaporator at 55° C./12–20 mm Hg. to give 3.12 g. of light brown colored oil. This was purified by chromatography on 100 g. of silica gel. Elution with ether = petroleum ether (1:3 parts by volume) afforded 1.796 g. of 2(R)-6-dimethyl-3(E)-heptenoic acid dimethylamide (49.0% yield).

EXAMPLE 3

Reaction of 6-methyl-2(E)-hepten-4(S)-ol with dimethylformamide dimethyl acetal 1.28 g. (10 mmol) of 6-methyl-2(E)-hepten-4(S)-ol (having 97.8% by weight S and about 2.2% by weight R) and 7.5 g. of dimethylformamide dimethyl acetal in 20 ml. of xylene were refluxed (124°–126° C.) for 70 hours under continuous removal of methanol. The solvent and excess of reagent were evaporated off at 60° C/0.20 mm Hg and the crude product was chromatographed on 30 g. of silica gel. Elution with ether = petroleum ether (1:4 parts by volume) gave 1.479 g. of beta-gamma-unsaturated amide. This was further purified by evaporative distillation to give a mixture containing 87.2% by weight of 2(R),6-dimethyl-3(E)-heptenoic acid dimethylamide and 12.8% by weight of 3(S),6-dimethyl-3(Z)-heptenoic acid dimethylamide (determined by nmr) as a colorless oil $[\alpha]_D^{25}$ −46.37° (c 5.0215, CHCl$_3$).

EXAMPLE 4

Preparation of 2(R),6-dimethylheptanoic acid dimethylamide 1.20 g. of 2(R),6-dimethyl-3(E)-heptenoic acid dimethylamide (95%R, 5% S) was hydrogenated in 50 ml. of ethylacetate at 220° C. in the presence of 120 mg. of 5% by weight palladium on 95% by weight charcoal. After 4.0 hours, no more hydrogen was absorbed and the catalyst was filtered off and washed with 50 ml. of ethyl acetate. The solvent was evaporated off to give 1.21 g. of colorless oil. This was distilled by evaporation at 82°–89° C./0.15 mm Hg. to yield 1.191 g. of pure 2(R),6-dimethylheptanoic acid dimethylamide, $[\alpha]_D^{25}$-27.14° (c 5.1148, CHCl$_3$).

EXAMPLE 5

From 1.10 g. of 2(R),6-dimethyl-3(E)-heptenoic acid dimethylamide (87.2% R, 12.8% S) and 110 mg. of 5% by weight palladium on 95% by weight charcoal, in 50 ml. of ethylacetate was hydrogenated at 23° C. and atmospheric pressure for 3.0 hours to give 1.07 g. of colorless oil, b.p. 83° C/0.13 mm Hg (Kugelrohr), $[\alpha]_D^{25}$−21.61° (C 5.0753, CHCl$_3$), nmr revealed a mixture of 84.6% by weight 2(R),6-dimethylheptanoic acid dimethylamide and 12.8% by weight 2(S),6-dimethyl-heptanoic acid dimethylamide.

EXAMPLE 6

Preparation of 2(R),6-dimethylheptanoic acid 538 mg. of 2(R),6-dimethylheptanoic acid and dimethylamide fro Example 4 in concentrated aqueous hydrochloric acid (10 ml.) was refluxed with stirring for 20 hours. After evaporating off the concentrated HCl at 45°–50° C./15–20 mm Hg, the oily residue was taken into 10% by weight aqueous NaOH. The aqueous phase was extracted with 3 × 20 ml. ether. The combined ether extract was washed with water, dried (MgSO$_4$) and evaporated to dryness to give 10 mg. of neutral material. The alkaline aqueous phase was then cooled in an ice-bath, and acidified with concentrated aqueous hydrochloric acid to Congo red. This was extracted with ether (3 × 50 ml.). The combined ether extract was washed with water, dried (MgSO$_4$) and evaporated to give 375 mg. (81.5% yield) of oil. Distillation (evaporative) at 82°–86° C./0.15 mm Hg gave 365 mg. of 2(R),6-dimethyl heptanoic acid as a colorless oil, $[\alpha]_D^{25}$=15.60° (c 4.9232, CHCl$_3$).

EXAMPLE 7

462 mg. of 2(R),6-dimethylheptanoic acid dimethylamide $[\alpha]_D^{25}$-21.61°, from Example 5 was refluxed with stirring in concentrated hydrochloric acid (10 ml.) for 20 hours. It was worked up as in Example 6 to give 248 mg. of colorless oil, b.p. 92°–95° C./0.20 mm Hg. (Kugelrohr), $[\alpha]_D^{25}$-12.80° (c. 5.0408, CHCl$_3$) which was a mixture containing 84.6% by weight 2(R),6-dimethylheptanoic acid and 12.4% by weight 2(S),6-dimethylheptanoic acid.

EXAMPLE 8

Preparation of 2(R),6-dimethylheptanoic acid methyl ester

2(R),6-dimethylheptanoic acid (300 mg. $[\alpha]_D^{25}$-15.6°, for Example 6 was dissolved in ether and treated with an excess of etheral diazomethane. The yellow solution was left at 23° C. overnight. Evaporation of ether (45°/20 mm Hg) to dryness gave 260 mg. of 2(R),6-dimethylheptanoic acid methyl ester, b.p. 114°–119°/45 mm Hg. (evaporative distillate), $[\alpha]_D^{25}$-20.10° (c. 1.1242, CHCl$_3$).

EXAMPLE 9

In a similar manner, 2(R),6-dimethylheptenoic acid (from Example 7, $[60]_D^{25}$-12.80°) was converted to a mixture containing 85% by weight of 2R,6-dimethylheptanoic acid methyl ester and 15% by weight of 2(S),6-dimethylheptanoic acid methyl ester (as determined by nmr).

EXAMPLE 10

Preparation of 2(R),6-dimethylheptanol-1

2(R),6-dimethylheptanoic acid and methyl ester (105 mg., $[\alpha]_D^{25}$-20.10°, from Example 8) and 100 mg. of LiAlH$_4$ in 15 ml. of ether were refluxed with stirring for 2 ½ hours. The reaction was cooled in an ice-bath and the excess of LiAlH$_4$ was destroyted by carefully adding water followed by 20 ml. of cold 2 N aqueous sulfuric acid. It was then extracted with ether (3 × 50 ml.) and combined ether extract was washed with water and dried (MgSO$_4$). Evaporation of ether to dryness and distillation of the crude product afforded 65 mg. of 2(R),6-dimethyl-heptanol-1 as a colorless oil, b.p. 130°/30 mm Hg. (evaporative distillate) $[\alpha]_D^{25}$+9.23° (c 1.1049, benzene).

EXAMPLE 11

6(R),10-dimethyl-2(Z)-undecen-4(R)-ol (1.54 g., 7.77 mmol) (having about 91.8% by weight R, and about 8.2% by weight S) and dimethylformamide dimethyl acetal (7.0 g., 58.8 mmol) in xylene (15 ml.) were refluxed at 124°–126° C. under continuous distillative removal of methanol for 93 hours. The xylene was evaporated off at reduced pressure and the crude product (2.20 g.) was chromatographed on 40.0 g. of silica gel. Elution with ether = petroleum ether (1:4 parts by volume) gave 0.815 g. of product (41.4% yield). This was distilled (evaporative distillation) at 116°–119°/0.15 mm Hg. to give pure 2(R),6(R),10-N,N-pentamethyl-3(E)-undecen-amide $[\alpha]_D^{25}$-43.70°.

EXAMPLE 12

1.45 g. (7.32 mmol) of 6(R),10-dimethyl-2(E)-undecen-4(S)-ol (having about 95% by weight S and 5% by weight R at C$_4$) and 7.0 g. of dimethylformamide dimethyl acetal in 15 ml. of xylene were refluxed for 93 hours as described in Example 11. The crude product was chromatographed on 40 g. of silica gel and elution with ether/petroleum ether (3:17 parts by volume) gave 1.22 g. (65.9% yield) of 2(R),6(R),10-N,N-pentamethyl-3(E,Z)-undecenamide after evaporation distillation, b.p. 138°–142°/0.22 mm Hg. $[\alpha]_D^{25}$-30.5° (c 4.9305, CHCl$_3$).

EXAMPLE 13

Preparation of 2(R),6(R),10-N,N-pentamethylundecanamide

2(R),6(R),10-N,N-pentamethyl-3(E)-undecenamide (636 mg.) and 75 mg. of 5% by weight palladium on 95% by weight charcoal in 25 ml. of ethyl acetate were hydrogenated at 23° C., 1 atmosphere for 4.0 hours. It was worked up in the manner of Example 4 and the product was distilled (evaporative distillation at 140°/0.5–0.7 mm Hg. to give 607 mg. of 2(R),6(R),10-N,N-penta-methyl-undecanamide as a colorless oil, $[\alpha]_D^{25}$-15.32° (C 5.2345, CHCl$_3$).

EXAMPLE 14

Preparation of 2(R),6(R),10-trimethylundecanoic acid

2(R),6(R),10-N,N-pentamethylundecanamide (415 mg., $[\alpha]_D^{25}$-15.32°) was refluxed with stirring in concentrated hydrochloric acid (10 ml.) for 24 hours. The reaction mixture was worked up as in Example 6 and the crude product was distilled (evaporate distillation) at 135°/0.15 mm Hg. to give 305 mg. of 2(R),6(R),10-trimethylundecanoic acid (82% yield) as a colorless oil, $[\alpha]_D^{25}$-8.64° (c 4.8382, CHCl$_3$).

EXAMPLE 15

Preparation of 2(R),6(R),10-trimethylundecanoic acid methyl ester

2(R),6(R),10-trimethylundecanoic acid (270 mg., $[\alpha]_D^{25}$-8.64°) was dissolved in ether and treated with an excess of etheral soluton of diazomethane at 23° C. for 2.0 hour. The crude product was subjected to evaporative distillation at 98°–101°/0.15 mm Hg to give 247 mg. of 2(R),6(R),10-trimethylundecanoic acid methyl ester as a colorless oil, $[\alpha]_D^{25}$-11.30° (c 1.1065, CHCl$_3$).

EXAMPLE 16

Preparation of 2(R),6(R),10-trimethylundecan-1-ol

2(R),6(R),10-trimethylundecanoic acid methyl ester (172 mg., $[\alpha]_D^{25}$-11.30°) and lithium aluminum hydride (170 mg.) in absolute ether (20 ml.) were refluxed with stirring for 2 ½ hours. The reaction mixture was cooled in an ice-bath and excess of hydride was destroyed by carefully adding water followed by 30 ml. of 1 N aqueous H$_2$SO$_4$. The aqueous phase was extracted with ether (3 × 40 ml.) and the combined ether extract was washed with water (3 × 30 ml.) and dried (MgSO$_4$). The crude product (155 mg.) was purified by evaporative distillation to give 152 mg. (100% yield) of 2(R),6(R),10-trimethylundecan-1-ol as a colorless liquid, b.p. 100°–102° C./0.08 mm Hg.; $[\alpha]_D^{25}$+ 6.09° C. (c 2.0366, hexane).

EXAMPLE 17

Preparation of 5-[2(S),6-benzyloxy-2,5,7,8-tetramethyl-2-chromanyl]-2(S),N,N-trimethyl-3(E)-pentenamide 2(S)-[2'(S)-hydroxy-3(Z)-pentenyl]-2,5,7,8-tetramethyl-6-benzyloxychroman (1.0 g., 2.63 mmol, $[\alpha]_D^{25}$-30.57°) and dimethylformamide dimethyl acetal. (2.2 g., 18.41 mmol) in xylene (10 ml.) were refluxed (130°–135° C.) under the continuous removal of methanol by distillation for 66 hours. The solvent and excess of reagent were removed in a rotary evaporator to give approximately 1.22 g. of brown colored viscous oil, which was purified by column chromatography on 40 g. of silica gel. Elution with ether = petroleum ether (1 = 9) gave 487 mg. of oil.

Further elution with ether = petroleum (55 = 45 parts by volume) then gave 520 mg. of 5-[2(S),6-benzyloxy-2,5,7,8-tetramethyl-2-chromanyl]-2(S),N,N-trimethyl-3(E)-pentenamide as a light yellow colored viscous oil, (45.5% yield) $[\alpha]_D^{25}+ 53.27°$ (c 3.634, CHCl$_3$).

EXAMPLE 18

2(S)-[2'(R)-hydroxy-3(E)-pentenyl]-2,5,7,8-tetramethyl-6-benzyloxychroman (1.09 g. $[\alpha]_D^{25}$- 24.02°) and dimethylformamide dimethyl acetal (2.2 g) in xylene (15 ml.) were refluxed for 62 hours as described in Example 17. The crude product was purified by chromatography on 30 g. of silica gel. Elution with ether - petroleum ether (1:1 parts by volume) gave 876 mg. (76.8% yield) of 5-[2'(S),6-benzyloxy-2,5,7,8-tetramethyl-2-chromanyl]-2(S)-N,N-trimethyl-3(E)-pentenamide as a light yellow viscous oil, $[\alpha]_D^{25}+ 43.94°$.

EXAMPLE 19

Preparation of 2(S)-[2(R)-hydroxy-3-pentynyl]-2,5,7,8-tetramethyl-6-benzyloxy-chroman and 2(S)-[2(S)-hydroxy-3-pentynyl]-2,5,7,8-tetramethyl-6-benzyloxy chroman To an excess of propynyl magnesium bromide (approximately 2.5 equivalents) in 1.0 l. of dry ether was added 64 g. (0.189 mol) of (S)-6-benzyloxy-2,5,7,8-tetramethylchroman-2-acetaldehyde in 1.0 l. of dry ether, at 0°-4° C. with mechanical stirring. When addition was complete the reaction mixture was further stirred at 0° C. for ½ hour and then at 25° C. for ½ hour. The reaction mixture was poured in small portions into 500 ml. of saturated aqueous NH$_4$Cl solution. It was extracted with diethyl ether (4 × 250 ml.). The combined ether extract was washed with water (3 × 200 ml.), dried over MgSO$_4$ and concentrated at reduced pressure. Crystallization of the crude product from diethyl ether - petroleum ether (30° – 60° C.) yielded 27.5 g. of 2(S)-[2(R)-hydroxy-3-pentynyl]-2,5,7,8-tetramethyl-6-benzyloxychroman, m.p. 89°–91° C., $[\alpha]_D^{25}$–16.05° (CHCl$_3$).

The mother liquor from above was concentrated to dryness and crystallized from ether - hexane to give 5.01 g. of 2(S)-[2(S)-hydroxy-3-pentynyl]-2,5,7,8-tetramethyl-6-benzyloxychroman as white crystals, m.p. 74°–76° C. $[\alpha]_D^{25}$–42.01°.

EXAMPLE 20

Preparation of 2(S)-[2(R)-hydroxy-3(E)-pentenyl]-2,5,7,8-tetramethyl-6-benzyloxychroman To a solution of 5.0 g. (13.32 mmol) of 2(S)-[2(R)-hydroxy-3-pentynyl]-2,5,7,8-tetramethyl-6-benzyloxychroman in 50 ml. of dry ether was carefully added 4.06 ml. of sodium bis(2-methoxyethoxy)-aluminum hydride (29 mg. - atm. of hydrogen) in 10 ml. of dry ether. The resulting solution was refluxed under Argon for 17 hours. The solution was cooled in an ice bath and 10% by volume aqueous H$_2$SO$_4$ solution (100 ml.) was carefully added. It was filtered, washed with ether and water. The aqueous phase was again extracted with ether (3 × 100 ml.). The combined ether phase was washed with saturated aqueous NaHCO$_3$ solution (3 × 50 ml.) and water (3 × 50 ml.) and dried over MgSo$_4$. Evaporation of ether to dryness at reduced pressure yielded 5.206 g. of crude product which was crystallized from petroleum ether (b.p. 30°-60° C.) to give 4.23 g. of 2(S)-[2(R)-hydroxy-3(E)-pentenyl]-2,5,7,8-tetramethyl-6-benzyloxychroman as white needles, m.p. 68°–70° C. $[\alpha]_D^{25}$-24.02° (CHCl$_3$).

EXAMPLE 21

Preparation of 2(S)-[2(S)-hydroxy-3(Z)-pentenyl]-2,5,7,8-tetramethyl-6-benzyloxychroman 2.5 g. of 2(S)-[2(S)-hydroxy-3-pentynyl]-2,5,7,8-tetramethyl-6-benzyloxychroman and 0.25 g. of Lindlar catalyst in 15 ml. of ethyl acetate-hexane (2 = 1 parts by volume) containing 0.1 ml. of quinoline was hydrogenated at 25° C. and atmospheric pressure. The catalyst was filtered off and washed with ethyl acetate. The ethyl acetate solution was washed with 1.0 N aqueous HCl (3 × 50 ml.), dried over MgSO$_4$ and concentrated in vacuo to give 2.508 g. of crude product. Crystallization of this material from pentane yielded 2.053 g. of 2(S)-[2(S)-hydroxy-3(Z)-pentenyl]-2,5,7,8-tetramethyl-6-benzyloxychroman as white crystalls, m.p. 84°–86° C. $[\alpha]_D^{25}$–30.57° (CHCl$_3$).

EXAMPLE 22

Preparation of 5-[2(R),6-benzyloxy-2,5,7,8-tetramethyl-2-chromanyl]-2(S)-methylpentanoic acid 5-[2(S),6-benzyloxy-2,5,7,8-tetramethyl-2-chromanyl]-2(S),N,N-trimethyl-3(E)-pentenamide was hydrogenated with 5% by weight palladium on 95% by weight charcoal as described in Example 5 to give 5-[2(R),6, benzyloxy-2,5,7,8-tetramethyl-2-chromanyl]-2(S)-methylpentanoic acid dimethylamide. This was refluxed with KOH in ethylene glycol for 17 hours and worked up in the manner described in Example 6 to give 5-[2(R),6-benzyloxy-2,5,7,8-tetramethyl-2-chromanyl]-2(S)-methylpentanoic acid.

EXAMPLE 23

Preparation of 5-[2(R),6-benzyloxy-2,5,7,8-tetramethyl-2-chromanyl]-2(S)-methylpentanol-1- and 5-[2(R),6-benzyloxy-2,5,7,8-tetramethyl-2-chromanyl]-2(S)-methylpentanol p-toluenesulfonate 5-[2(R),6-benzyloxy-2,5,7,8-tetramethyl-2-chromanyl]-2(S)-methylpentanoic acid was reduced to 5-[2(R),6-benzyloxy-2,5,7,8-tetramethyl-2-chromanyl]-2(S)-methylpentanol-1with lithium aluminum hydride as described in Example 10. This material (0.01 mol) was dissolved in dry pyridine (30 ml.) and cooled in an ice-bath. To the solution was added 0.02 mol. of p-toluenesulfonyl chloride in portions. The resulting mixture was kept at 0° C. for 20 hours then treated with ice-water. The precipitated oily material was extracted with ether and the ether extracts were combined, washed with cold 1 N aqueous HCl, saturated aqueous NaHCO$_3$, and water, then dried over anhydrous K$_2$CO$_3$–Na$_2$SO$_4$. After filtration and removal of solvent in vacuo, there was obtained 5-[2(R),6-benzyloxy-2,5,7,8-tetramethyl-2-chromanyl]-2(S)-methylpentanol p-toluenesulfonate as a yellow oil.

EXAMPLE 24

(2R,4'R,8'R)- α-tocopheryl benzyl ether

A solution of 3(R),7-dimethyloctyl magnesium bromide (10 mmol) in dry tetrahydrofuran (20 ml.) was added dropwise, with stirring to a solution of 5-[2(R),6-benzyloxy-2,5,7,8-tetramethyl-2-chromanyl]-2(S)-methylpentanol p-toluenesulfonate (7.7 mmol) in tetrahydrofuran (10 ml.) cooled to −78° C. After the addition of 0.4 ml. of 0.1 M dilithium tetrachlorocuprate solution in tetrahydrofuran, the reaction mixture was stirred for 10 minutes at −78° C, then for 2 ½ hours at 0°–5° C. and finally at 23° C. for 17 hours. Aqueous 1 N H$_2$SO$_4$ was added and the mixture was extracted with ether. The combined ether extract was washed with water and dried over anhydrous MgSO$_4$. Evaporation of ether to dryness in vacuo gave (2R,4'R,8'R)-α-tocopheryl benzyl ether as a viscous oil.

EXAMPLE 25

(2R,4'R,8'R)- α-tocopherol (2R,4'R,8'R)-α -tocopherol benzyl ether (5 mmol) was hydrogenated in 50 ml. of ethyl acetate at 23° C, atmospheric pressure, in the presence of 1.0 g. of 5% by weight palladium on 95% by weight carbon catalyst. After the uptake of hydrogen stopped, the catalyst was filtered off and washed well with ethyl acetate. The solvent was concentrated in vacuo to give (2R,4'R,-8'R)- α -tocopherol as a colorless, viscous oil, shown to be identical with an authentic sample.

We claim:

1. A process for producing a compound of the formula

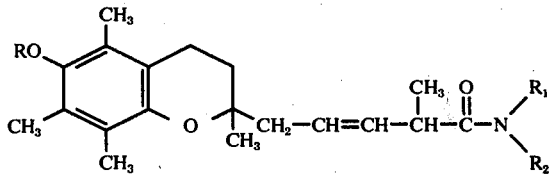

wherein R is benzyl, trialkyl silyl, t-butyl, benzhydryl, trityl, tetrahydropyranyl, alpha-lower alkoxy-lower alkyl; and R$_1$ and R$_2$ are lower alkyl;
comprising reacting at a temperature of from 100° C to 400° C in an inert organic solvent medium a compound of the formula:

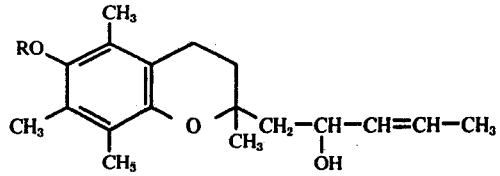

wherein R is as above; with a compound of the formula:

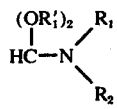

wherein R$_1$ and R are as above; and R$_1'$ is lower alkyl.

2. The process of claim 1 wherein a compound of the formula

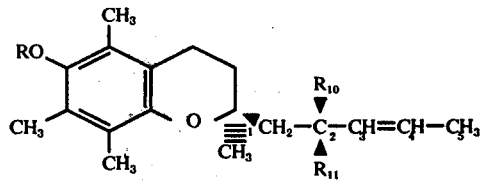

wherein R is as above; one of R$_{10}$ and R$_{11}$ is hydroxy and the other is hydrogen; with the proviso that when R$_{10}$ is hydroxy, the 3–4 double bond is cis and when the R$_{10}$ is hydrogen, the 3–4 double bond is trans; is reacted with a compound of the formula:

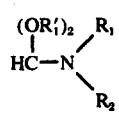

wherein R$_1'$, R$_1$ and R$_2$ are as above; to produce a compound of the formula:

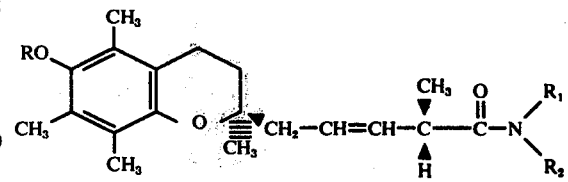

wherein R, R$_1$ and R$_2$ are as above.

* * * * *